(12) United States Patent
Chebath et al.

(10) Patent No.: US 6,172,042 B1
(45) Date of Patent: Jan. 9, 2001

(54) SYNTHETIC PEPTIDES THAT INHIBIT IL-6 ACTIVITY

(75) Inventors: Judith Chebath, Rehovot (IL); Robert Halimi, Strassbourg (FR); Michel Revel, Rehovot (IL)

(73) Assignee: Yeda Research and Development Co. LTD, Rehovot (IL)

( * ) Notice: Under 35 U.S.C. 154(b), the term of this patent shall be extended for 0 days.

(21) Appl. No.: 09/043,785
(22) PCT Filed: Sep. 26, 1996
(86) PCT No.: PCT/IL96/00119
§ 371 Date: Sep. 2, 1998
§ 102(e) Date: Sep. 2, 1998
(87) PCT Pub. No.: WO97/13781
PCT Pub. Date: Apr. 17, 1997

(30) Foreign Application Priority Data

Sep. 28, 1995 (IL) .......... 115453
May 1, 1996 (IL) .......... 118097

(51) Int. Cl.⁷ .......... A61K 38/04; A61K 38/08
(52) U.S. Cl. .......... 514/15; 514/14; 530/326; 530/327
(58) Field of Search .......... 514/14, 15; 530/326, 530/327

(56) References Cited

PUBLICATIONS

"Remington Pharmaceutical Sciences", part 8, Mack Publishing Co., Easton, PA, 1980.*

Grube et al, "Indentification of a Regulatory Domain of the Interleukin–6 Receptor", *J. Biol. Chem.* 269(32):20791–20797 (1994).

Halmi et al, "Epitope peptides from interleukin–6 receptor which inhibit the growth of human meyloma cells", *Eur. Cytokine Netw.* 6(3):134–143 (1995).

Weiergraber et al, "Use of immobilized synthetic peptides for the identification of contact sites between human interleukin–6 and its receptor", *FEBS Letters* 379(2):122–126 (1996).

* cited by examiner

Primary Examiner—Michael Borin
(74) Attorney, Agent, or Firm—Browdy and Neimark

(57) ABSTRACT

Novel peptides derived from the gp80 subunit of the IL-6 receptor system which inhibit the activity of IL-6 are provided.

25 Claims, 6 Drawing Sheets

```
: EPITOPES OF McAB 34.4 AND 50.6 IN IL-6 RECEPTOR gp80

223    230       240         250       260        270
TVT AVARNPRWLSVTWQDPHSWN S SFYRLRFELRYRAERSKTFTTWMV KD
    1086                     1062
                                       1063
```

PEPTIDES RECOGNIZED ON SPOT-SCAN

| McAB 34.4 | 67 | LRYRAERSKT | ++ |
| | 68 | YRAERSKTFT | +++ |
| | 69 | AERSKTFTTW | ++ |
| | 70 | RSKTFTTWMV | ++ |
| | 71 | KTFTTWMVKD | + |

| McAB 50.6 | 63 | SFYRLRFELR | + |
| | 64 | YRLRFELRYR | ++ |
| | 65 | LRFELRYRAE | +++ |

ALIGNEMENTS IL-6R and HGHR

Bold residues for ligand binding
Italic residues for HGHR dimerization
Circles: mutation impairing IL-6 binding Epitopes of McABs

```
              121                    134                   144      151
               oo                     o
IL-6R   PPEEPQLSCFRKS|P|LSNVVCEWGPRSTPSL |· |TTKAVLLVRKFQN
HGHR    SKEPKFTKCRSPE|  |RETFSCHWTDEVHHGTK|*|LGPIQLFYTRRNT
              25       38   43        48                          70

160        170     180            190
                                       oo             oo
IL-6R     |SP|AEDFQEPCQYSQESQ|KFSCQLAVPEG |DSSFYIVSMCVASS|
HGHR      |**|WTQEWKECPDYVSAG|ENSCYFNSSFTS|IWIPYCIKLTSNGG|

218
                                   ooo
IL-6R        VGSKFSKTQTFQGCGIL|QPDPPA
HGHR         TVDEKCFSVDEIV|QPDPPI                    McAB50.6     McAB34.4

238                   251      258
        221    226       233     o o         o      o  oo    oooo
IL-6R   NITVTAVA|  RN  |PRWLSVTWQDPHSWNSS|  |FYRLRFELRYRAERS
HGHR    ALNWTLLN|*SLT**|HADIQVRWEAPRNADIQ|K*|WMVLEYELQYKEVNE
                                                  165      169

267  270      277   282   287      295        0000000
                          oo         o   oo  oo    oo
IL-6R    |KTFTTWMVKDLQH|   |HCVIHDAWS|GLRHVVQLRAQEEF|GQGEWSEWS
HGHR     | TKWKMMDPILTT|   |SVPVYSLKV|DKEYEVRVRSKQR |NSGNYGEFS 309    314
             o      o
IL-6R    PEAMGT PWTESRSPP
HGHR     EVLYVTLPQMSQFT
```

Figure 1

FIG. 2 : EPITOPES OF McAB 34.4 AND 50.6 IN IL-6 RECEPTOR gp80

```
223      230          240           250          260          270
     TVTAVARNPRWLSVTWQDPHSWNSSFYRLRFELRYRAERSKTFTTWMVKD
        |1086                 | |1062        |
                                         |   1063      |
```

PEPTIDES RECOGNIZED ON SPOT-SCAN

| McAB 34.4 | 67 | LRYRAERSKT | ++ |
|---|---|---|---|
| | 68 | YRAERSKTFT | +++ |
| | 69 | AERSKTFTTW | ++ |
| | 70 | RSKTFTTWMV | ++ |
| | 71 | KTFTTWMVKD | + |
| McAB 50.6 | 63 | SFYRLRFELR | + |
| | 64 | YRLRFELRYR | ++ |
| | 65 | LRFELRYRAE | +++ |

Figure 2

SEQUENCE LISTING

```
<160> NUMBER OF SEQ ID NOS: 4

<210> SEQ ID NO 1
<211> LENGTH: 210
<212> TYPE: PRT
<213> ORGANISM: Human

<400> SEQUENCE: 1

Pro Pro Glu Glu Pro Gln Leu Ser Cys Phe Arg Lys Ser Pro Leu Ser
  1               5                  10                  15

Asn Val Val Cys Glu Trp Gly Pro Arg Ser Thr Pro Ser Leu Thr Thr
             20                  25                  30

Lys Ala Val Leu Leu Val Arg Lys Phe Gln Asn Ser Pro Ala Glu Asp
         35                  40                  45

Phe Gln Glu Pro Cys Gln Tyr Ser Gln Glu Ser Gln Lys Phe Ser Cys
```

-continued

```
                 50                      55                      60
Gln Leu Ala Val Pro Glu Gly Asp Ser Ser Phe Tyr Ile Val Ser Met
 65                      70                      75                      80

Cys Val Ala Ser Ser Val Gly Ser Lys Phe Ser Lys Thr Gln Thr Phe
                         85                      90                      95

Gln Gly Cys Gly Ile Leu Gln Pro Asp Pro Ala Asn Ile Thr Val
                    100                     105                     110

Thr Ala Val Ala Arg Asn Pro Arg Trp Leu Ser Val Thr Trp Gln Asp
                115                     120                     125

Pro His Ser Trp Asn Ser Ser Phe Tyr Arg Leu Arg Phe Glu Leu Arg
                130                     135                     140

Tyr Arg Ala Glu Arg Ser Lys Thr Phe Thr Thr Trp Met Val Lys Asp
145                     150                     155                     160

Leu Gln His His Cys Val Ile His Asp Ala Trp Ser Gly Leu Arg His
                    165                     170                     175

Val Val Gln Leu Arg Ala Gln Glu Glu Phe Gly Gln Gly Glu Trp Ser
                180                     185                     190

Glu Trp Ser Pro Glu Ala Met Gly Thr Pro Trp Thr Glu Ser Arg Ser
                195                     200                     205

Pro Pro
    210

<210> SEQ ID NO 2
<211> LENGTH: 204
<212> TYPE: PRT
<213> ORGANISM: Human

<400> SEQUENCE: 2

Ser Lys Glu Pro Lys Phe Thr Lys Cys Arg Ser Pro Glu Arg Glu Thr
  1               5                      10                      15

Phe Ser Cys His Trp Thr Asp Glu Val His His Gly Thr Lys Leu Gly
                 20                      25                      30

Pro Ile Gln Leu Phe Tyr Thr Arg Arg Asn Thr Trp Thr Gln Glu Trp
                 35                      40                      45

Lys Glu Cys Pro Asp Tyr Val Ser Ala Gly Glu Asn Ser Cys Tyr Phe
 50                      55                      60

Asn Ser Ser Phe Thr Ser Ile Trp Ile Pro Tyr Cys Ile Lys Leu Thr
 65                      70                      75                      80

Ser Asn Gly Gly Thr Val Asp Glu Lys Cys Phe Ser Val Asp Glu Ile
                    85                      90                      95

Val Gln Pro Asp Pro Pro Ile Ala Leu Asn Trp Thr Leu Leu Asn Ser
                100                     105                     110

Leu Thr His Ala Asp Ile Gln Val Arg Trp Glu Ala Pro Arg Asn Ala
                115                     120                     125

Asp Ile Gln Lys Trp Met Val Leu Glu Tyr Glu Leu Gln Tyr Lys Glu
                130                     135                     140

Val Asn Glu Thr Lys Trp Lys Met Met Asp Pro Ile Leu Thr Thr Ser
145                     150                     155                     160

Val Pro Val Tyr Ser Leu Lys Val Asp Lys Glu Tyr Glu Val Arg Val
                    165                     170                     175

Arg Ser Lys Gln Arg Asn Ser Gly Asn Tyr Gly Glu Phe Ser Glu Val
                180                     185                     190

Leu Tyr Val Thr Leu Pro Gln Met Ser Gln Phe Thr
                195                     200
```

```
<210> SEQ ID NO 3
<211> LENGTH: 26
<212> TYPE: PRT
<213> ORGANISM: Human

<400> SEQUENCE: 3

Pro Gly His Arg Tyr Arg Asp Gln Gln Thr Gln Thr Ser Phe Ser Glu
 1               5                  10                  15

Glu Pro Gln Ser Ser Gln Leu Leu Pro Cys
            20                  25

<210> SEQ ID NO 4
<211> LENGTH: 6
<212> TYPE: PRT
<213> ORGANISM: Human

<400> SEQUENCE: 4

Arg Ala Gln Glu Glu Phe
 1               5
```

SYNTHETIC PEPTIDES THAT INHIBIT IL-6 ACTIVITY

FIELD OF THE INVENTION

The present invention is generally in the field of inhibitors of Interleukin-6 (IL-6) activity. More specifically, the present invention concerns new synthetic peptides which are capable of inhibiting the IL-6-dependent growth of myeloma/plasmacytoma cells.

BACKGROUND OF THE INVENTION AND PRIOR ART

The receptor system for Interleukin-6 (IL-6) is composed of two distinct receptor subunits designated gp80 (IL-6R) and gp130 (reviewed in Hirano et al., 1994). These two receptor proteins belong to the cytokine receptor superfamily of Bazan (1990). The 3-dimensional structure of the human Growth Hormone Receptor (hGHR), a member of this family, has been revealed by crystallography (DeVos et al., 1992), from which the residues which interact with the ligand and those which mediate the interaction between the two receptor subunits in their extracellular domains, have been determined. The alignment of part of the amino acid sequence of the extracellular domain of the IL-6R and hGHR sequences based on Bazan's model is shown schematically in FIG. 1.

IL-6 is a pleiotropic cytokine which has a number of important biological activities (see Revel, 1992, for review). Further, IL-6 has been implicated in the growth and progression of human multiple myeloma (Klein et al., 1990).

In fact, IL-6 is a growth factor for B-lymphocyte leukemic cells of Multiple Myeloma. These leukemic cells are also called plasmacytoma or myeloma cells, as they are derived from mature B-lymphocytes or plasma cells. When fused to antibody-producing B-cells, these myeloma or plasmacytoma cells are called hybridoma cells.

In view of the fact that IL-6 is a growth factor for such plasmacytoma or myeloma cells, there has been a long-felt need to obtain specific IL-6 inhibitors which may be used to block the IL-6-mediated or IL-6-dependent growth of such plasmacytoma/myeloma cells, and thereby provide a way for treating Multiple Myeloma, a disease affecting a very large number of people worldwide. To this end, Grube and Cochrane (1994) have described a peptide derived from IL-6R, called peptide 249–264 (i.e. a peptide having the amino acid residues from residue No. 249 to residue No. 264 of the IL-6R amino acid sequence), which is capable of inhibiting the growth of murine plasmacytoma B9 cells. It is also known that IL-6 plays a role in the inhibition of other diseases, such as osteoporosis and autoimmune diseases.

Heretofore, neither the specific peptides of the present invention, nor their specific biological activities and other characteristics such as, for example, their specificity for certain monoclonal antibodies, have been described.

It is therefore an aim of the present invention to provide new peptides derived from IL-6R which are capable of inhibiting the IL-6-dependent growth of human myeloma or murine plasmacytoma cells.

It is another aim of the present invention to provide such new peptides which are further characterized by virtue of their defining linear epitopes within the IL-6R sequence, which are the binding sites of monoclonal antibodies (Mabs) which are themselves capable of blocking IL-6 activity.

Yet another aim of the invention is to provide a chemical synthesis process for the preparation of the new peptides.

A yet further aim of the invention is to provide pharmaceutical compositions containing the new peptides.

SUMMARY OF THE INVENTION

The present invention is based on the unexpected finding that short peptides within the IL-6 receptor gp80 molecule (IL-6R) could be defined by virtue of their ability to bind two different monoclonal antibodies (Mabs) which were previously known to strongly inhibit the activity of IL-6. Further, when chemically synthetized, in accordance with the present invention, these peptides when added to cultures of leukemic cells, were surprisingly shown to be capable of causing the complete inhibition of the growth of such leukemic (plasmacytoma/myeloma) cells.

Accordingly, the present invention provides a peptide or biologically active analogs thereof capable of inhibiting the activity of IL-6, wherein said peptide is characterized by being derived from the gp80 (IL-6R) subunit of the IL-6 receptor system and by being a linear epitope recognized by one or more monoclonal antibodies (Mab) specific to IL-6R, with the proviso that said peptide is other than the group of peptides consisting of: (i) the 16 amino acid peptide having the amino acid sequence of residues 249–264 of the IL-6R molecule; (ii) the 14 amino acid peptide having the amino acid sequence of residues 255–268 of the IL-6R molecule; (iii) the 6 amino acid peptide having the amino acid sequence of residues 249–254 of the IL-6R molecule; (iv) the 10 amino acid peptide having the amino acid sequence of residues 259–268 of the IL-6R molecule; and (v) the 10 amino acid peptide having the amino acid sequence of residues 249–258 of the IL-6R molecule.

An embodiment of the above peptide or analogs thereof of the invention is a peptide selected from the group of peptides having between about 4 and about 25 amino acid residues derived from the portion of the IL-6R molecule extending between residue 223 and residue 272 as depicted in FIG. 2, said group of peptides comprising:

(a) a peptide having at least the 10 amino acid sequence LRYRAERSKT from position 255 to position 264 of the IL-6R molecule (residues 143–152 of SEQ ID NO:1);

(b) a peptide having at least the 10 amino acid sequence YRAERSKTFT from position 257 to position 266 of the IL-6R molecule (residues 145–154 of SEQ ID NO:1);

(c) a peptide having at least the 10 amino acid sequence AERSKTFTTW from position 259 to position 268 of the IL-6R molecule (residues 147–156 of SEQ ID NO:1);

(d) a peptide having at least the 10 amino acid sequence RSKTFTTWMV from position 261 to position 270 of the IL-6R molecule (residues 149–158 of SEQ ID NO:1);

(e) a peptide having at least the 10 amino acid sequence KTFTTWMVKD from position 263 to position 272 of the IL-6R molecule (residues 151–160 of SEQ ID NO:1);

(f) a peptide having at least the 10 amino acid sequence SFYRLRFELR from position 247 to position 256 of the IL-6R molecule (residues 135–144 of SEQ ID NO1);

(g) a peptide having at least the 10 amino acid sequence YRLRFELRYR from position 249 to position 258 of the IL-6R molecule (residues 137–146 of SEQ ID NO:1);

(h) a peptide having at least the 10 amino acid sequence LRFELRYRAE from position 251 to position 260 of the IL-6R molecule (residues 139–148 of SEQ ID NO:1); and (i) an analog of any one of the peptides of (a)–(h) in which one or more amino acid residues have been added, deleted or substituted by another amino acid residue, and wherein said peptides and analogs of (a)–(i) are characterized by defining all or part of a linear epitope recognized by anti-IL-6R monoclonal antibodies and by being capable of inhibiting IL-6 activity.

Another embodiment of the above peptides or analogs of the invention is a peptide or analog wherein said peptide or analog defines a linear epitope recognized by one or both of the Mabs, herein designated Mab 34.4 and Mab 50.6.

A yet further embodiment of the above peptides of the invention is a peptide selected from any one of the herein designated peptides: (i) 1062 having the sequence from position 247 to position 260 of the IL-6R molecule as depicted in FIG. 2; (ii) 1063 having the sequence from position 255 to position 270 of the IL-6R molecule as depicted in FIG. 2; (iii) 1086 having the sequence from position 226 to position 245 of the IL-6R molecule as depicted in FIG. 2; (iv) 1085 having the sequence from position 234 to position 245 of the IL-6R molecule as depicted in FIG. 2; and (v) 1122 having the sequence from position 260 to position 269 of the IL-6R molecule as depicted in FIG. 2.

The present invention also provides in another aspect, a peptide or biologically active analogs thereof capable of inhibiting IL-6 activity, wherein said peptide is characterized by being derived from the gp80 (IL-6R) subunit of the IL-6 receptor system and by being part of all of the region of IL-6R that is involved in the binding to IL-6, with the proviso that said peptide is other than the group of peptides consisting of: (i) the 16 amino acid peptide having the amino acid sequence of residues 249–264 of the IL-6R molecule; (ii) the 14 amino acid peptide having the amino acid sequence of residues 255–268 of the IL-6R molecule; (iii) the 6 amino acid peptide having the amino acid sequence of residues 249–254 of the IL-6R molecule; (iv) the 10 amino acid peptide having the amino acid sequence of residues 259–268 of the IL-6R molecule; and (v) the 10 amino acid peptide having the amino acid sequence of residues 249–258 of the IL-6R molecule.

An embodiment of this aspect of the invention is a peptide selected from the herein designated peptides:

(a) 983 having the sequence from position 277 to position 299 of the IL-6R molecule as depicted in Table 1;

(b) 1064 having the sequence from position 290 to position 300 of the IL-6R molecule as depicted in Table 1;

(c) 1067 having the sequence from position 125 to position 135 of the IL-6R molecule as depicted in Table 1; and (d) an analog of any one of (a)–(c) wherein one or more amino acids have been added, deleted or substituted by another amino acid.

The invention also provides a pharmaceutical composition comprising as active ingredient at least one of the above peptides, analogs or mixtures of any thereof and a pharmaceutically acceptable carrier, diluent or excipient.

Embodiments of the pharmaceutical composition of the invention include a pharmaceutical composition for the inhibition of IL-6 and a pharmaceutical composition for the treatment of Multiple Myeloma, osteoporosis and autoimmune diseases.

In addition, the present invention also provides for the use of the above peptides, analogs or mixtures of any thereof for the preparation of any of the above pharmaceutical compositions, or for the inhibition of IL-6, or for the treatment of Multiple Myeloma osteoporosis and autoimmune diseases.

Other aspects of the invention are set forth or arise directly from the following detailed description of the invention.

BRIEF DESCRIPTION OF THE DRAWINGS

FIG. 1 shows schematically a comparison of part of the amino acid sequence of the extracellular domain of the IL-6R molecule, i.e., residues 113–322 (SEQ ID NO:1) of IL-6R, with that of the human Growth Hormone Receptor (hGHR, i.e., residues 25–241 (SEQ ID NO:2) of hGHR). The alignment of the sequences is according to Bazan (1990). The position of the epitopes for Mab 34.4 and 50.6 are shown by flags in the figure.

FIG. 2 shows schematically a segment of the IL-6R amino acid sequence (residues 111–160 of SEQ ID NO:1) in which the limits of the three peptides, designated herein 1086, 1062 and 1063, are depicted by the boxes (upper part of the figure). The reaction of various overlapping decapeptides (residues 143–152, 145–154, 147–156, 149–158, 151–160, 135–144, 137–146 and 139–148 of SEQ ID NO:1, respectively) with Mabs is depicted in the lower part of the figure, the decapeptides having sequences contained with the 1086, 1062 and 1063 peptides. In this lower part, the numbers refer to the position of each peptide on the membrane grid (spot-scan test), and the "+" symbols denote the relative intensity of the reactions (positive results), all as described in Examples 1–3.

DETAILED DESCRIPTION OF THE INVENTION

Figure 3:
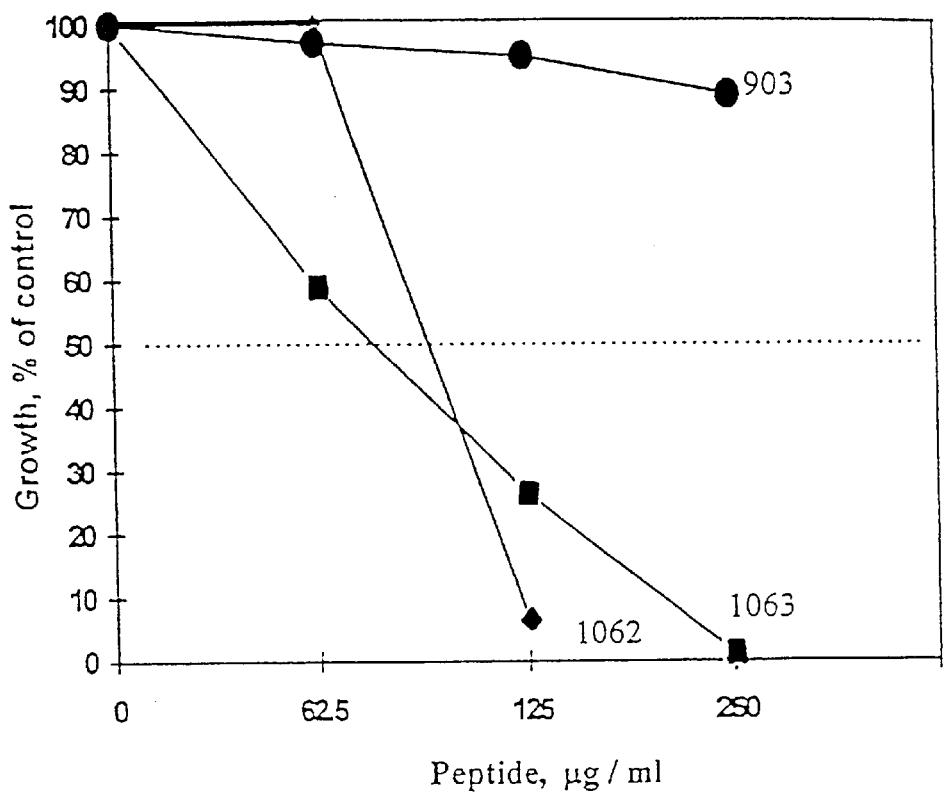
FIG. 3 shows graphically the effects of peptides 1062, 1063 and control peptide 903 (see Table 1) on the growth of B9 plasmacytoma-derived cells which is dependent on IL-6 addition. Recombinant CHO-produced human IL-6 was used at 2.5 U/ml (i.e. 7.5 IU/ml) and the growth measured after 3 days. Peptides were added at indicated concentration together with IL-6. All as described in Examples 2 and 3.

The present invention concerns in one aspect new peptides which are capable of inhibiting the activity of IL-6, which are characterized as being derived from the gp 80 (IL-6R) subunit of the IL-6 receptor system and as being linear epitopes recognized by one or more monoclonal antibodies (Mab) specific to IL-6R.

IL-6 is a growth factor for B-lymphocyte leukemic cells of Multiple Myeloma, i.e. plasmacytoma or myeloma cells. In accordance with the present invention, the above new peptides, being short peptides within the IL-6R molecule were defined by their ability to bind two Mabs previously isolated and characterized (Novick et al., 1992) as being Mabs which strongly inhibited the activity of IL-6. These new peptides were synthesized chemically and added to cultures of such leukemic cells and were observed to cause the complete inhibition of the growth of such plasmacytoma/myeloma cells.

Thus, the new peptides or mixtures of two or more such peptides of the invention may be used in a general fashion for the inhibition of IL-6 and for the inhibition of IL-6-mediated cellular activities, when such activities are undesired. For example, when IL-6 is produced intracellularly in abnormally large amounts or when IL-6 is administered in large doses, and in both situations the IL-6 reaches undesirably high levels in the body, giving rise to undesirable side effects, the peptides or mixtures thereof according to the invention may be used. Alternatively, the new peptides individually or mixtures of two or more thereof may be used specifically for the treatment of diseases such as, for example, Multiple Myeloma in humans in which the growth of the cancerous cells constituting this disease (B-lymphocyte leukemic cells) is dependent of IL-6. In this application, the new peptides of the invention antagonize the binding of IL-6 to its receptor or interfere with the function of the receptor system which transduces, intracellularly, molecular signals leading to the growth of myeloma cells.

Of the above new peptides, preferred peptides are those having between about 4 and about 25 amino acid residues derived from the IL-6R molecule and which define linear epitopes recognized by either of the anti-IL-6R Mabs 34.4 and 50.6 (both Mabs being potent inhibitors of IL-6 activity). Of these preferred peptides are included:

(a) a peptide having at least the 10 amino acid sequence LRYRAERSKT from position 255 to position 264 of the IL-6R molecule (residues 143–152 of SEQ ID NO:1);

(b) a peptide having at least the 10 amino acid sequence YRAERSKTFT from position 257 to position 266 of the IL-6R molecule (residues 145–154 of SEQ ID NO:1);

(c) a peptide having at least the 10 amino acid sequence AERSKTFTTW from position 259 to position 268 of the IL-6R molecule (residues 147–156 of SEQ ID NO:1);

(d) a peptide having at least the 10 amino acid sequence RSKTFTTWMV from position 261 to position 270 of the IL-6R molecule (residues 149–158 of SEQ ID NO:1);

(e) a peptide having at least the 10 amino acid sequence KTFTTWMVKD from position 263 to position 272 of the IL-6R molecule (residues 151–160 of SEQ ID NO1);

(f) a peptide having at least the 10 amino acid sequence SFYRLRFELR from position 247 to position 256 of the IL-6R molecule (residues 135–144 of SEQ ID NO:1);

(g) a peptide having at least the 10 amino acid sequence YRLRFELRYR from position 249 to position 258 of the IL-6R molecule (residues 137–146 of SEQ ID NO:1);

(h) a peptide having at least the 10 amino acid sequence LRFELRYRAE from position 251 to position 260 of the IL-6R molecule residues 139–148 of SEQ ID NO:1.

Further, the above preferred peptides also include any of the herein designated peptides: (i) 1062 having the sequence from position 247 to position 260 of the IL-6R molecule as depicted in FIG. 2; (ii) 1063 having the sequence from position 255 to position 270 of the IL-6R molecule as depicted in FIG. 2; (iii) 1086 having the sequence from position 226 to position 245 of the IL-6R molecule as depicted in FIG. 2; (iv) 1085 having the sequence from position 234 to position 245 of the IL-6R molecule as depicted in FIG. 2, and (v) 1122 having the sequence from position 260 to position 269 of the IL-6R molecule as depicted in FIG. 2.

Moreover, it should be noted that in accordance with the present invention, the use of Mabs to define, isolate and characterize peptides which represent linear epitopes recognized by the Mabs on the IL-6R molecule, provides a new way in which to define and isolate peptides which are directly involved in the function of the IL-6R protein, for example peptides, such as those of the invention, which can interfere with the function of this protein, i.e. inhibit the activity of IL-6 (which is mediated by IL-6R). This use of Mabs is strikingly significant in view of the previous observations that the binding of Mabs to proteins is most often due to the recognition of a configuration within the protein and more rarely due to a recognition of a linear segment of the amino acid sequence of the protein.

In another aspect, the present invention also concerns new peptides which are capable of inhibiting the activity of IL-6 which are characterized by being derived from the gp80 (IL-6R) subunit of the IL-6 receptor system and by being part or all of the region of the IL-6R that is involved in the binding to IL-6.

Thus, these other new peptides, while not being defined and isolated by virtue of their being linear epitopes recognized by known Mabs, nevertheless represent peptides which antagonize the binding of IL-6 to its receptor or interfere with the function of the receptor system which transduces, intracellularly, molecular signals leading to the growth of IL-6-dependent cells, e. g. myeloma cells. Accordingly, these peptides may be used in the same way as noted above, i.e. for the inhibition of IL-6 activity in general, when said inhibition is desired, or specifically for the inhibition of IL-6-dependent cancerous cells such as in Multiple Myeloma in humans.

Of these other new peptides, preferred peptides include:

(a) 983 having the sequence from position 277 to position 299 of the IL-6R molecule as depicted in Table 1;

(b) 1064 having the sequence from position 290 to position 300 of the IL-6R molecule as depicted in Table 1;

(c) 1067 having the sequence from position 125 to position 135 of the IL-6R molecule as depicted in Table 1.

In yet another aspect, the present invention concerns biologically active analogs of any of the above noted new peptides. Suitable analogs are those which retain the ability to inhibit IL-6 activity by antagonizing the binding of IL-6 to its receptor or by interfering with the function of the receptor system which transduces, intracellularly, molecular signals leading to the growth of IL-6-dependent cells, such as, for example, myeloma cells. Of these suitable analogs are also included analogs which retain the essential amino acid residues of the linear epitopes recognized by the Mabs 34. 4 and 50. 6. These analogs of the invention are those which have at least one amino acid residue added, deleted or substituted by another amino acid when compared to the peptide amino acid sequence from which the analog amino acid sequence has been generated.

By virtue of the above characteristics of the analogs of the invention, these analogs may thus be used in the same way as the new peptides of the invention, i.e. as inhibitors of IL-6 activity in general or as agents for the treatment of IL-6-dependent cancerous cell growths, e. g. Multiple Myeloma.

The peptides and the analogs of the invention may be prepared by any well known procedure of the art, in particular, by the well established chemical synthesis procedures utilizing automated peptide synthesizers followed by chromatographic purification (see Example 2).

In a further aspect, the invention also concerns pharmaceutical compositions containing as active ingredient any of the above new peptides, analogs or mixtures of two or more peptides or analogs, as well as any of the well known pharmaceutically acceptable carriers, diluents or excipients.

These pharmaceutical compositions may be formulated for any form of administration as desired, for example, for intravenous, intraperitoneal or oral administration. Accordingly, the choice of diluent, carrier or excipient will be made according to the desired mode of administration.

The actual mode of administration and the optimal formulation therefor will be determined by skilled practitioners. Likewise, the dosage for administration and hence, the concentration of the active ingredient in each dosage form according to its mode of administration, will also be decided by skilled practitioners. However, in this regard it is considered that a suitably effective dosage form, for any route of administration, will be one that will result in a concentration in the body of about 50–100 $\mu$M of the peptides, analogs or mixtures thereof, following administration.

The pharmaceutical compositions of the invention may be used for the inhibition of IL-6 when such treatment is indicated, as noted above in cases where IL-6 levels are abnormally high, or they may be used specifically to treat such diseases where the diseases tissue is IL-6 dependent, for example, in Multiple Myeloma, in which the myeloma cells constituting the malignant growth are IL-6 dependent.

The present invention will now be described in more detail in the following non-limiting Examples, and the accompanying drawings.

EXAMPLE 1

Epitopes recognized by Mab 34.4 and 50.6

Monoclonal antibodies 34. 4 and 50. 6, previously prepared and characterized by a group including one of the present inventors, were shown to inhibit the binding of IL-6 to the gp80 subunit of the IL-6 receptor (IL-6R) and consequently to inhibit IL-6 binding to human cells and its biological activity (Novick et al., 1992).

The two antibodies 34. 4 and 50. 6 were studied in accordance with the present invention as regards their ability to recognize linear peptides from the IL-6R extracellular domain. For this purpose, using standard chemical synthesis procedures (see also Example 2), a series of 96 decapeptides were synthesized which span residues 123–322 of the IL-6R sequence. Each consecutive peptide was offset by 2 amino acids from the previous one, yielding a nested, overlapping library (see IL-6R sequence in FIG. 1 and some of the peptides as shown in FIG. 2). A membrane carrying the 96 peptides was reacted with Mab 34.4 (18 $\mu$g/ml) and stained with a $\beta$-galactosidase-conjugated secondary antibody (anti-mouse immunoglobulin antibody). Two series of $\beta$-galactosidase positive spots on the membrane were seen, one corresponding to residues 223–240 and the other to residues 241–272. A similar experiment was performed using a horseradish peroxidase-conjugated secondary antibody and detection by enhanced chemiluminescence (ECL kit, amersham Radiochemicals, UK). This method of detection is more quantitative and allowed for a comparison of the intensity of the reaction between the antibody and the diverse peptides. A strong reaction was observed with 4 peptide spots (67, 68, 69 and 70) corresponding to amino acids 255–264, 257–266, 259–268 and 261–270. These results are depicted in FIG. 2, which shows schematically a segment of the IL-6R amino acid sequence in which the limits of the three peptides designated herein as 1086, 1062 and 1063 are depicted by boxes (upper part of the figure) and which also shows the results of reaction of the various overlapping decapeptides contained within peptides 1086, 1062 and 1063 with Mabs (lower part of the figure). In these reaction results, the numbers refer to the position of each peptide on the membrane grid (spot-scan test) and the "+" symbols denote the extent of the reaction (+++=very strong reaction; ++=strong reaction; and +=fairly strong rection). Thus, from these results, it appears that the core of the epitope from Mab 34.4 is RSKT (261–264) but probably extends to further residues around this core.

In a similar way, the 96-peptide library of IL-6R was also tested with Mab 50.6 with the ECL detection method. Spots 64 and 65 reacted most strongly indicating sequence 251–258 as the core epitope for this second neutralizing antibody (FIG. 2).

EXAMPLE 2

Synthetic peptides corresponding to epitopes defined by Mab 34.4 and 50.6 inhibit the biological activity of IL-6 on hybridoma cell growth The region of the IL-6R sequence to which the neutralizing Mab 34.4 and 50.6 bind was determined as noted above (FIG. 2). The indicated peptides 1062 (IL-6R resdiues 257–260) 1063 (255–270) and 1086 (226 and 245) were obtained by solid-phase synthesis with a peptides synthesizer from Applied Biosystems (Foster City, Calif.). Purity of the peptides was verified by Reverse Phase High Performance Liquid Chromatography (RP-HPLC) on an Aquapore CB column (Brownlee).

These purified peptides were then tested for their ability to interfere with IL-6 action on cells. The rationale was that since the antibodies blocking IL-6 activity bind to epitope sequences within these peptides, it is likely that these sequences are important for some protein-protein interactions within the receptor complex. Hence, these peptides could themselves mimick such interactions and interfere with the normal protein-protein contacts necessary for the function of the receptor system.

To assay the biological activity of the peptides as inhibitors of IL-6 action against growth of plasmacytoma cells, a hybridoma cell line B9 whose growth is IL-6 dependent (Helle et al, 1988) was used. The B9 cells were cultured in suspension in growth medium RPMI 1640 (Biolabs Ltd., Israel) with 10% heat-inactivated fetal calf serum and 4 U/ml IL-6. The recombinant human IL-6 from Chinese Hamster Ovary (CHO) cells was a pure preparation as described (Novick et al., 1989) which titrated on T1165 plasmacytoma cells $5 \times 10^6$ units/mg (corresponding to 1.5×10$^7$ International units/mg).

Units used here are T1165 units (1 unit=3 International units).

Prior to assay, the B9 cells were washed and incubated for 5 hours in growth medium but without IL-6. The cells were centrifuged, resuspended in growth medium with 2.5 units/ml (i.e. 7.5 IU/ml) of IL-6 and seeded in a 96-well microplate (Nunc, Denmark) at 50,000 cells in a final volume of 0.2 ml per well. A 25 gl of water solution with appropriate peptide concentration was included in the final volume of each well, i.e. the peptides at concentrations ranging from 62.5 µg/ml to 250 µg/ml (as well as a 0 µg/ml control) were added together with the IL-6. After 3 days of culture at 37° C., a solution of Alamar Blue (Biosource, Camarillo, Calif.) was added at 20 µg/ml per well and after mixing, incubation was continued for 3 hours. The optical absorbance at 530 nm wavelength of each well was measured as specified by the manufacturer. The absorbance is directly proportional to the number of living cells in the well as verified in calibration experiments from 50,000 to $10^6$ B9 cells (0.25 OD530 corresponding to $5 \times 10^5$ B9 cells under the present experimental conditions). The results were expressed as the difference between final cell density with IL-6 and without IL-6. The IL-6 dependent difference in the absence of peptide was defined as 100% growth.

Figure 4:
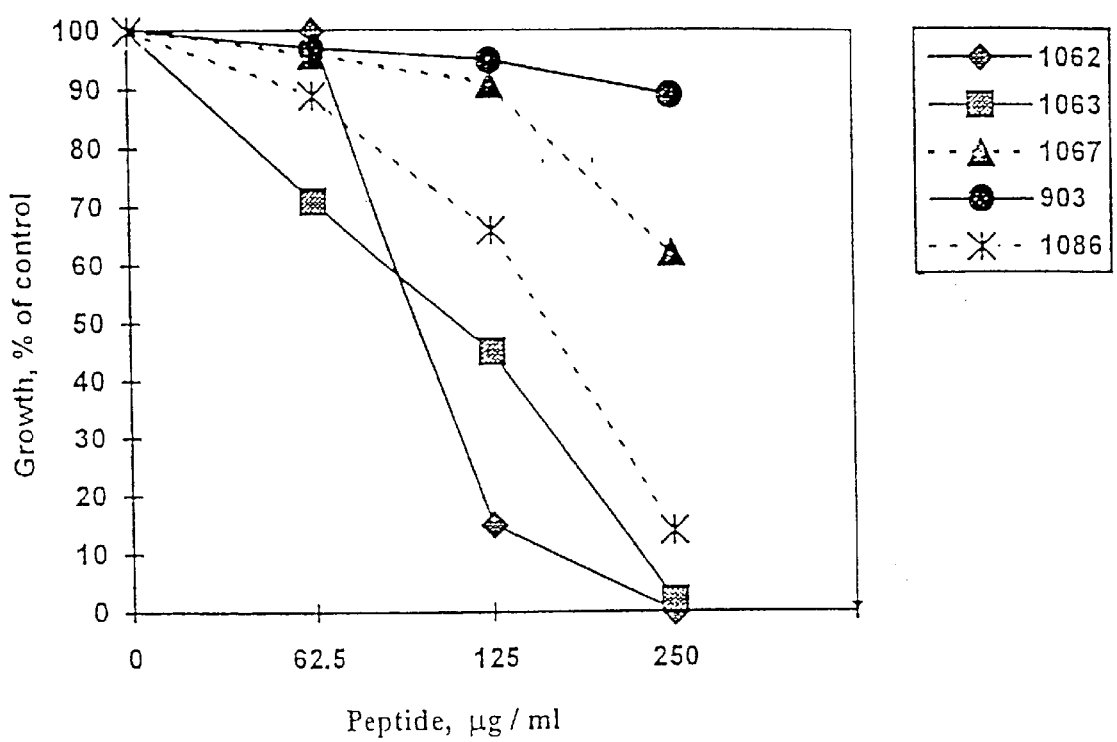
FIG. 4 shows graphically the effects of peptides 1062, 1063, 1067, 1086 and control peptide 903 (see Table 1) on growth of B9 plasmacytoma-derived cells, as described in Example 3.

The results of the above experiments are given in FIG. 4, which shows graphically the effects of peptides 1062, 1063 and control peptide (see below and Table 1) on the IL-6-dependent growth of the B9 plasmacytoma-derived cells. As is apprent from these results, the addition of increasing concentrations of peptide 1063 (255–270) resulted in a dose dependent inhibition of the growth of the B9 cells. At the highest dose, the growth inhibition was 99%. A complete inhibition was also obtained with peptide 1062 (257–260) but with a different dose curve. In contrast, a control peptide, 903 (with an unrelated sequence as shown in Table 1 below), did not inhibit the IL-6 dependent growth of the B9 cells. Therefore, the two peptides 1062 and 1063 corresponding to the core epitopes of the neutralizing Mabs 34. 4 and 50. 6 are potent specific inhibitors of the IL-6-dependent growth of plasmacytoma-derived cells.

TABLE 1

Peptides tested for inhibition of IL-6 activity and their coordinates in IL-6R

| Peptide | Sequence | Coordinates | Remarks | Residues of SEQ ID NO:1 |
|---|---|---|---|---|
| 1062 | SFYRLRFELRYRAE | 247–260 | Mab 50.6 epitope | 135–148 |
| 1063 | LRYRAERSKTFTTWMV | 255–270 | Mab 34/4 epitope | 143–158 |
| 983 | CVIHDAWSGLRHVVQLRAQEEFG | 277–299 | | 165–187 |
| 1064 | VQLRAQFEFCQ | 290–300 | IL-6 binding | 178–188 |
| 1067 | SPLSNVVCEWG | 125–135 | N-domain start | 13–23 |
| 1085 | LSVTWQDPHSWN | 234–245 | | 122–133 |
| 1086 | AVARNPRWLSVTWQDPHSWN | 226–245 | gp 130 interaction? | 114–133 |
| 903 | PGHRYRDQQTQTSFSEEPQSSQLLPC | other protein | control peptide | SEQ ID NO:2 |

The activity of peptide 1063 (255–270, Mab 34.4 epitope) was tested in 5 separate experiments and the inibition at the three doses was statistically highly significant (Table 2 below). Direct comparison of peptide 1063 to control peptide 903 showed a highly significant inhibition of the IL-6 dependent growth of the plasmacytoma derived B9 cells even when peptide 1063 was used at half the concentration of the control peptide (see legend of Table 2 below).

TABLE 2

IL-6 Antagonist activity of peptide from Mab 34.4 and 50.6 epitopes

| | IL-6 DEPENDENT HYBRIDOMA B9 CELL GROWTH | | |
|---|---|---|---|
| PEPTIDE | 62.5 µg/ml | 125 µg/ml | 250 µg/ml |
| | Percent of IL-6 dependent cell growth ± SD | | |
| 1063 (255–270) | 71 ± 9 (p = 0.001) | 45 ± 16 (p < 0.001) | 2 ± 1 (p < 0.0001) |
| 1062 (257–260) | 100 ± 0 (n.s.) | 15 ± 9 (p < 0.0001) | |
| 903 (control) | 97 ± 4 (n.s.) | 95 ± 9 (n.s.) | 89 ± 15 (n.s.) |

Statistical analysis of 5 experiments using two-tailed Student's t-test in comparison to no peptide. comparison of B9 cell growth with peptide 1063 and 125 µg/ml to control peptide 903 at 250 µg/ml was highly significant at p=0.004.

EXAMPLE 3

Comparison of peptides from Mab 34.4 and 50.6 epitopes to peptides from other regions of the IL-6R sequence for inhibition of hybridoma B9 cell growth.

Five peptides were prepared as noted above (Example 2) corresponding to different regions of the IL-6R sequence (see Table 1 above). Peptides 983 and 1064 correspond to a region homologous to that which in hGHR is involved in ligand binding (FIG. 1; DeVos et al., 1992) and which contains the RAQEEF (SEQ ID NO:4) motif shown to bind IL-6 (Martin et al., 1994). Peptide 1067 also corresponds to a region which in the hGHR molecule is involved in ligand binding (FIG. 1). Peptide 1086 corresponds to a region which has been shown to interact with gp130 (Savino et al., 1994) and is close to the epitope of Mab 34.4 and 50.6 (FIG. 2). These peptides were tested for their effect on the IL-6 dependent growth of the plasmacytoma-derived B9 cells, as in Example 2.

A comparison of the residual IL-6 dependent growth (see Table 3 below) shows that overlapping peptides 983 and 1064 were not active as compared to peptide 1063 (255–270). Peptide 1067 did show some activity but lower than peptide 1063. In a series of four experiments, the residual growth in the presence of peptide 1067 was 62% ±43 and was not significant statistically. However, peptide 1086 (226–245) did show activity, although lower than that of peptides 1062 and 1063. FIG. 4 shows graphically the effects of peptides 1062, 1063, 1067 and 1086 as compared to each other and to control peptide 903, on the growth of B9 plasmacytoma-derived cells. The results shown are the mean results of 4 experiments.

Figure 5:
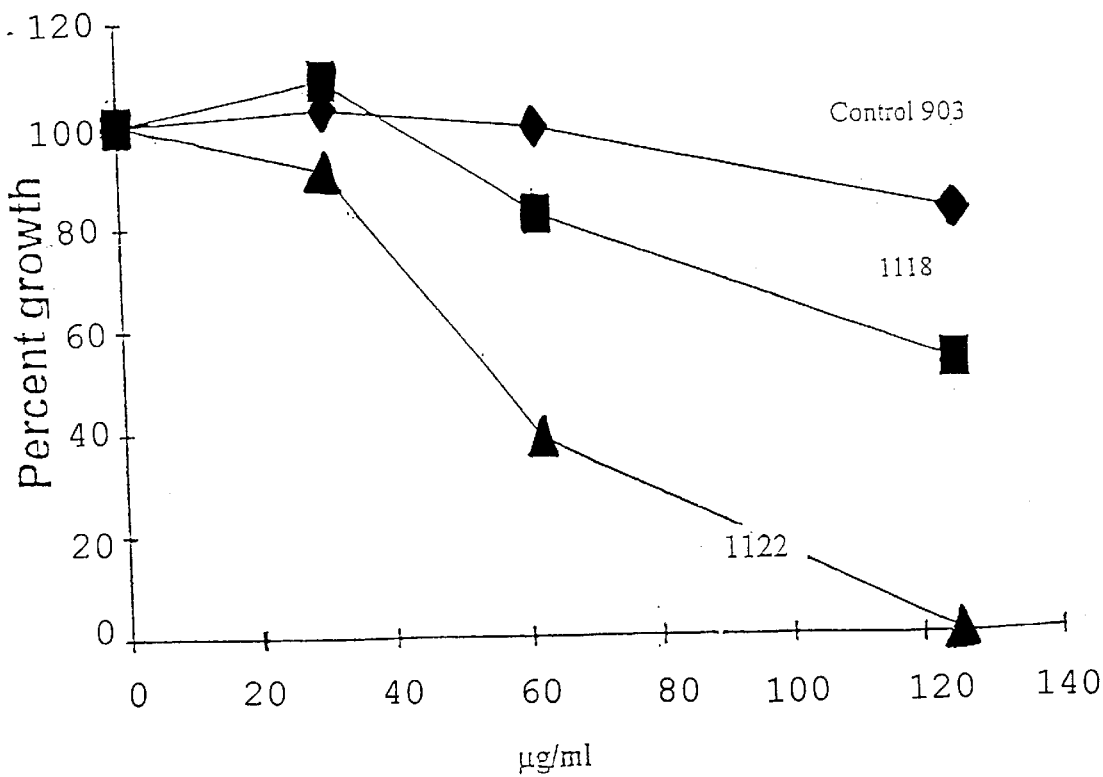
FIG. 5 shows the sequences and effects of peptides 1062, 1063, 1122, 1118 and control peptide 903 on growth of B9 plasmacytoma-derived cells, as described in Example 3. The sequences at the top of FIG. 5 represent residues 135–173, 135–148, 143–158, 137–142, 148–157, 147–156 and 162–173 of SEQ ID NO:1, respectively.

FIG. 5 shows again the sequences of the above mentioned peptides 1062 and 1063, and their effect on the growth of B9 plasmacytoma-derived cells, as well as those of peptide 1118 and 1122, having low, and strong effect, respectively, and those of two related peptides found to be inactive.

TABLE 3

Comparison of different peptides

| | HYBRIDOMA B9 CELL GROWTH WITH PEPTIDE | | | | |
|---|---|---|---|---|---|
| | 1063 | 1064 | 983 | 1067 | 903 |
| | Percent of IL-6 dependent cell growth | | | | |
| IL-6: 1 U/ml | 3% | 74% | 100% | 48% | 100% |

Peptides tested at 250 µg/ml

Figure 6:
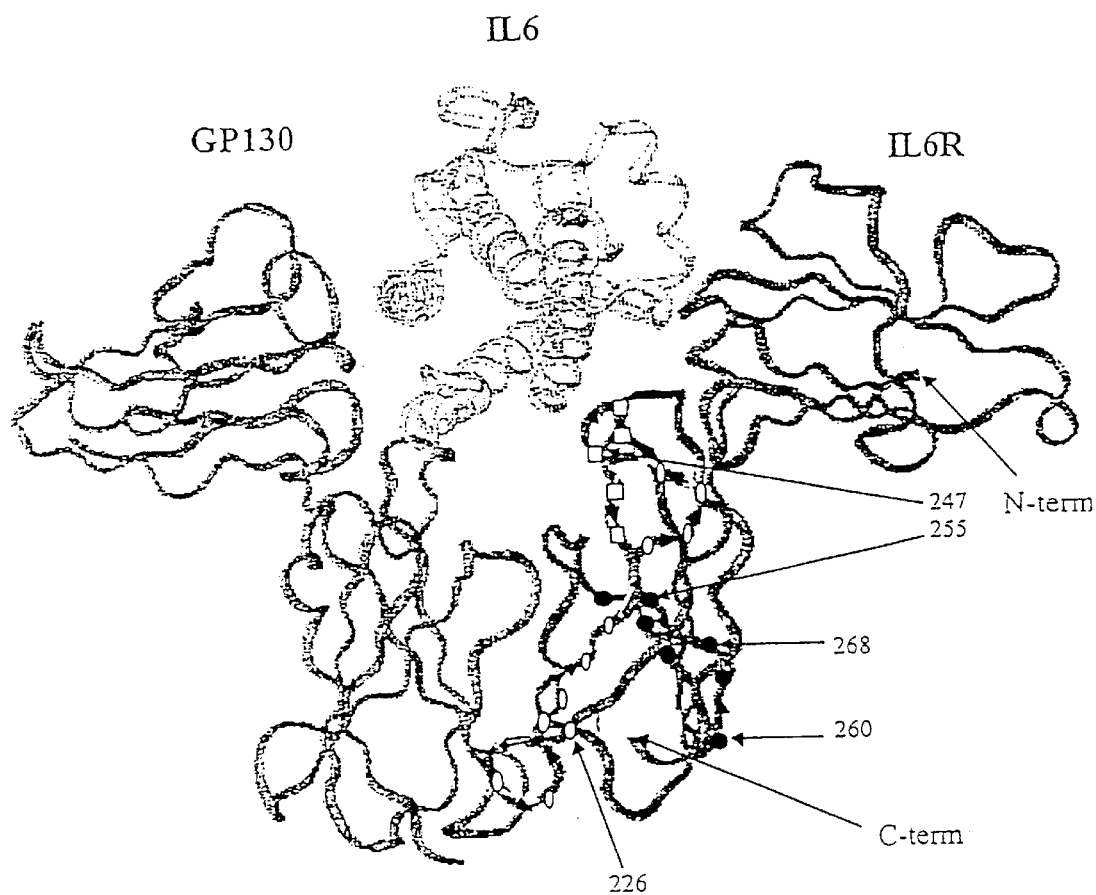
FIG. 6 shows graphically a three-dimensional model of the IL-6 receptor complex comprising IL-6R, gp 130 and the IL-6 ligand. This model was computed on the basis of the crystallographic data of DeVos et al (1992) for hGHR. The position of peptide 1063 is shown by filled circles and the direction of the strands by empty arrows. Part of peptides 1062 is shown by open squares and peptides 1086 by open elipses. All as also described in Example 3.

A three-dimensional model of the IL-6R molecule was produced based on the crystallographic coordinates of hGHR. This is shown schematically in FIG. 6, which is a three-dimensional model of the IL-6R complex comprising IL-6R, gp130 and the IL-6 ligand. This model was computed on the basis of the crystallographic data of DeVos (1992) for hGHR. The position of the different peptides tested is indicated. Peptide 1063 (255–270, marked by filled circles) does not appear to interact with the IL-6 ligand. Peptide 1062 (247–260, marked by open squares in the region preceding its overlap with peptide 1063) does contain residues around position 247 which could interact with IL-6. Peptide 1086 (226–245, marked by open elipses) contains a loop which interacts with gp130. It is known that gp130 dimerizes as a result of IL-6 and IL-6R binding (Hirano et al., 1994) and the IL-6R may similarly dimerize to form a hexameric complex. Building a computer model of this hexameric complex by a symetric assembly of two of the trimeric complexes shown in FIG. 6, revealed that peptide 1063 and part of 1062 are engaged in a second interaction of IL-6R and gp130. Therefore, the regions common to the active peptides, in particular peptide 1063 which is the most active inhibitor of IL-6, appear to interfere with the interactions between IL-6R and gp130 to form the hexameric complex, and hence inhibit the function of the IL-6 receptor complex.

EXAMPLE 4

Peptides defined by the Mab 34.4 and 50.6 epitopes inhibit the IL-6 dependent growth of human myeloma cells Multiple myeloma is a leukemia of plasma cells in which IL-6 is considered as a promoting growth factor (Klein et al., 1990). It was, therefore, of interest to determine if the peptides derived from the epitopes Mab 34.4 and 50.6, or other peptides, would inhibit the growth of such tumor cells. The XG-1 cell line has been established from a patient with multiple myeloma (Klein et al., 1990) and the growth of these cells is dependent on the addition of IL-6. Cultures of XG-1 cells were established in 6-well Costar plates, in a final volume of 1 ml. The cells were cultured with or without IL-6 (0.2 U/ml, i.e. 0.6 IU/ml) for 3 days and then pulsed with tritium-labeled thymidine for 2 hours. The incorporation of radioactive thymidine was used as a measure of DNA replication and growth. As indicated in Table 4 below, the IL-6 dependent growth was strongly reduced (by 85%) by the addition of 100 µg/ml of peptide 1062, and was reduced by more than 55% with peptide 1063. In contrast peptide 1064, gave only a small inhibitory effect. Peptide 1067 was found also to be active to inhibit the growth of these human myeloma cells (see Table 4 below).

Therefore, the IL-6R peptides are capable of inhibiting the function of the human IL-6 receptor complex in human tumor cells.

TABLE 4

Effect on human myeloma XG-1 cells

| | HUMAN MYELOMA XG-1 GROWTH WITH PEPTIDE | | | | |
|---|---|---|---|---|---|
| | none | 1062 | 1063 | 1064 | 1067 |
| | $^3$H-Thymidine incorporation, cpm × $10^{-3}$ | | | | |
| No IL-6 | 6.4 ± 1.6 | 8.3 ± 0.3 | 8.7 ± 2.5 | 10.1 ± 0.3 | 6.5 ± 1.9 |
| IL-6, 0.2 U/ml | 43.6 ± 0.9 | 15.1 ± 3.3 | 25.2 ± 0.2 | 39.1 ± 1.5 | 10.7 ± 0.3 |
| IL-6 dpdt (%) | 37.2 (100) | 6.8 (18.2) | 16.5 (44.3) | 29.0 (78) | 4.2 (11.3) |

In view of the results set forth herein above (Examples 1–4), a comparison was made between these results ("Present Invention") and the previously reported results concerning peptides described by Cochrane (Grube and Cochrane, 1994, "Prior Art"). This comparative analysis is set forth in Table 5 below. It should be noted that Cochrane showed only peptide 249–264 (Y249–T264) to be active on the B9 lymphocytoma-derived cells, whilst the other peptides described by Cochrane were tested on HepG2 cell for effects on fibrinogen secretion. In contrast, the peptides of the present invention 1062 (247–260), 1063 (255–270) and 1086 (226–245), which all differ (although with some overlap as regards 1062 and 1063) from those of Cochrane, have been shown to be active on B9 cells. Moreover, peptides 1062 and 1063 inhibit human myeloma XG-1 cells. Furthermore, the most similar peptides (although still being different) of the present invention and of Cochrane, namely 1063 (255–270) and 255–268, respectively, are also different in activity. The peptide of the present invention, 1063 (L255–V270) has been shown in accordance with the invention to be active on B9 cells whilst that of Cochrane (255–268) tested on HepG2 cells was inactive.

Finally, the peptides prepared and characterized according to the present invention have been isolated by the initial procedure of epitope mapping using the previously prepared Mabs 34.4 and 50.6. In contrast, Cochrane prepared the peptides by random synthesis of different peptides.

TABLE 5

Comparison between the activity of the peptides of the present invention and those of the prior art (Grube and Cochrane, 1994)

| Present Invention | | | Prior Art | | |
|---|---|---|---|---|---|
| | RESULT | | | RESULT | |
| PEPTIDE | B9 cells | XG-1 | PEPTIDE | B9 cells | HepG2 |
| 247–260 (1062) | active | active | 249–264 | active | active |
| 255–270 (1063) | active | somewhat | 255–268 | not done | inactive |
| | | | 249–254 | not done | inactive |
| | | | 259–268 | not done | inactive |
| | | | 249–258 | not done | active |
| 226–245 (1086) | active | not done | | | |

References

Bazan J. F. (1990) Structural design and molecular evolution of a cytokine receptor superfamily. Proc. Natl. Acad. Sci. USA 87:6934–6938.

De Vos A. M., Ultsch M. and Kossiakoff A. A. (1992) Human Growth Hormone and extracellular domain of its receptor:crystal structure of the complex. Science 255:306–312.

Grube B. J. and Cochrane C. G. (1994), Identification of a regulatory domain of the Interleukin-6 receptor. J. Biol. Chem. 269:20791–20797.

Helle M., Boije L. and Aarden L. (1988) Functional discrimination between Interleukin-6 and Interleukin-1. Eur. J. Inmnunol. 18:1535–1540.

Hirano T., Matsuda T. and Nakajima K. (1994) Signal transduction through gp130 that is shared among the receptors for the Interleukin-6 related cytokine subfamily. Stem Cells 12:262–277.

Klein B., Zhang X. G., Jourdan M., Boiron J. M., Portier M., Lu Z. Y., Wijdenes J., Brochier J. and Bataille R. (1990) Interleukin-6 is the central tumor growth factor in vitro and in vivo in multiple myeloma. Eur. Cyt. Netw. 1: 193–201.

Martin F., Toniatti C., Salvati A. L., Venturini S., Ciliberto G., Cortese R. and Sollazzo M. (1994) The affinity selection of a minibody polypeptide inhibitor of human IL-6. EMBO J. 13:5303–5309.

Novick D., Eshhar Z., Revel M. and Mory Y. (1989) Monoclonal antibodies for affinity purification of IL-6/IFN-β2 and for neutralization of HGF activity. Hybridoma 8:561–567.

Novick D., Shulman L. M., Chen L. and Revel M. (1992) Enhancement of Interleukin-6 cytostatic effect on human breast carcinoma cells by soluble IL-6 receptor from urine and reversion by Monoclonal Antibody. Cytokine 4:6–11.

Revel M. (Ed.) IL-6:*Physiopathology and clinical potentials*. Serono Symposia Publications, Vol. 88, Raven Press, New York, 1992.

Savino R., Ciapponi L., Lahm A., Demartis A., Cabibbo A., Toniatti C., Delmastro P., Altmura S. and Ciliberto G. (1994) Rational design of a receptor superantagonist human IL-6. *EMBO J.* 13:5863–5870.

We claim:

1. A peptide capable of inhibiting the activity of IL-6, which peptide is selected from the group consisting of the sequences of the following residue ranges of SEQ ID NO:1: 135–148; 143–158; 13–23; 122–133; 114–133; and 148–157.

2. A peptide in accordance with claim 1 consisting of the sequence of residues 135–148 of SEQ ID NO:1.

3. A peptide in accordance with claim 1 consisting of the sequence of residues 143–158 of SEQ ID NO:1.

4. A peptide in accordance with claim 1 consisting of the sequence of residues 13–23 of SEQ ID NO:1.

5. A peptide in accordance with claim 1 consisting of the sequence of residues 122–133 of SEQ ID NO:1.

6. A peptide in accordance with claim 1 consisting of the sequence of residues 114–133 of SEQ ID NO:1.

7. A peptide in accordance with claim 1 consisting of the sequence of residues 148–157 of SEQ ID NO:1.

8. A pharmaceutical composition comprising as active ingredient one peptide or a mixture of two or more peptides according to claim 1, and a pharmaceutically acceptable carrier, diluent or excipient.

9. A pharmaceutical composition comprising, as active ingredient, the peptide in accordance with claim 2, and Et pharmaceutically acceptable carrier, diluent or excipient.

10. A pharmaceutical composition comprising, as active ingredient, the peptide in accordance with claim 3, and a pharmaceutically acceptable carrier, diluent or excipient.

11. A pharmaceutical composition comprising, as active ingredient, the peptide in accordance with claim 4, and a pharmaceutically acceptable carrier, diluent or excipient.

12. A pharmaceutical composition comprising, as active ingredient, the peptide in accordance with claim 5, and a pharmaceutically acceptable carrier, diluent or excipient.

13. A pharmaceutical composition comprising, as active ingredient, the peptide in accordance with claim 6, and a pharmaceutically acceptable carrier, diluent or excipient.

14. A pharmaceutical composition comprising, as active ingredient, the peptide in accordance with claim 7, and a pharmaceutically acceptable carrier, diluent or excipient.

15. A method for the treatment of a disease or condition associated with IL-6 activity comprising administering to a patient an effective amount of one or more peptides in accordance with claim 1 in an amount effective to inhibit IL-6 activity.

16. A method in accordance with claim 15 wherein the disease or condition being treated is multiple myeloma.

17. A method for inhibiting IL-6 activity comprising administering to a patient in need thereof an effective amount of one or more peptides in accordance with claim 1.

18. A method for inhibiting IL-6 activity comprising administering to a patient in need thereof an effective amount of a peptide in accordance with claim 2.

19. A method for inhibiting IL-6 activity comprising administering to a patient in need thereof an effective amount of a peptide in accordance with claim 3.

20. A method for inhibiting IL-6 activity comprising administering to a patient in need thereof an effective amount of a peptide in accordance with claim 4.

21. A method for inhibiting IL-6 activity comprising administering to a patient in need thereof an effective amount of a peptide in accordance with claim 5.

22. A method for inhibiting IL-6 activity comprising administering to a patient in need thereof an effective amount of a peptide in accordance with claim 6.

23. A method for inhibiting IL-6 activity comprising administering to a patient in need thereof an effective amount of a peptide in accordance with claim 7.

24. A method in accordance with claim 15, wherein the disease or condition being treated is osteoporosis.

25. A method in accordance with claim 15, wherein the disease or condition being treated is an autoimmune disease associated with IL-6 activity.

* * * * *

UNITED STATES PATENT AND TRADEMARK OFFICE
CERTIFICATE OF CORRECTION

PATENT NO. : 6,172,042 B1
DATED : January 9, 2001
INVENTOR(S) : Chebath et al.

It is certified that error appears in the above-identified patent and that said Letters Patent is hereby corrected as shown below:

Column 17,
Line 48 (claim 9, line 2), delete "Et" and insert therefor -- a --.

Signed and Sealed this

Twenty-third Day of October, 2001

Attest:

NICHOLAS P. GODICI
Attesting Officer      Acting Director of the United States Patent and Trademark Office